US007201922B2

(12) United States Patent
Serpelloni

(10) Patent No.: US 7,201,922 B2
(45) Date of Patent: Apr. 10, 2007

(54) ORODISPERSIBLE SOLID PHARMACEUTICAL FORM

(75) Inventor: Michel Serpelloni, Beuvry-les-Bethune (FR)

(73) Assignee: Roquette Freres, Lestrem (FR)

(*) Notice: Subject to any disclaimer, the term of this patent is extended or adjusted under 35 U.S.C. 154(b) by 146 days.

(21) Appl. No.: 10/167,016

(22) Filed: Jun. 11, 2002

(65) Prior Publication Data

US 2003/0147947 A1 Aug. 7, 2003

(30) Foreign Application Priority Data

Jan. 18, 2002 (FR) .................................. 02 00647

(51) Int. Cl.
*A61K 9/14* (2006.01)
*A61K 9/20* (2006.01)
*A61K 9/28* (2006.01)
*A61K 9/50* (2006.01)

(52) U.S. Cl. ...................... 424/489; 424/464; 424/474; 424/499

(58) Field of Classification Search ................ 424/464, 424/465
See application file for complete search history.

(56) References Cited

U.S. PATENT DOCUMENTS

| 4,327,077 | A | * | 4/1982 | Puglia et al. ................ 424/441 |
| 5,464,632 | A | | 11/1995 | Cousin et al. |
| 5,587,172 | A | * | 12/1996 | Cherukuri et al. ........... 424/401 |
| 5,679,685 | A | * | 10/1997 | Cincotta et al. ............. 514/288 |
| 6,106,861 | A | | 8/2000 | Chauveau et al. |
| 6,287,596 | B1 | * | 9/2001 | Murakami et al. ........... 424/464 |
| 6,316,029 | B1 | * | 11/2001 | Jain et al. .................... 424/484 |
| 6,723,348 | B2 | | 4/2004 | Faham et al. |
| 6,770,368 | B2 | * | 8/2004 | Luhn .......................... 428/403 |
| 2002/0035248 | A1 | | 3/2002 | Luhn |
| 2003/0099700 | A1 | * | 5/2003 | Faham et al. ................ 424/465 |
| 2003/0118642 | A1 | * | 6/2003 | Norman et al. .............. 424/465 |
| 2003/0165563 | A1 | * | 9/2003 | Murphy et al. .............. 424/465 |
| 2003/0215502 | A1 | * | 11/2003 | Pruss et al. .................. 424/465 |
| 2004/0014680 | A1 | * | 1/2004 | Nakagami et al. ............ 514/23 |
| 2004/0265380 | A1 | * | 12/2004 | Delmas et al. .............. 424/466 |
| 2005/0131071 | A1 | * | 6/2005 | Wuthrich et al. ............ 514/630 |

FOREIGN PATENT DOCUMENTS

WO 00/57857 10/2000

OTHER PUBLICATIONS

U.S. Appl. No. 10/341,178.*
Webster's II, New Colleged Dictionary. p. 448.*
"On the direct compression of sulfamethoxydiazine (SMD) polymorphic forms", Conte U. et al., Il Farmaco Edizione Pratica, vol. 30, No. 4, Apr. 1975, pp. 194-206.
Pharmeuropa, vol. 10, No. 4, Dec. 1998, pp. 547-549.
Derwent Abstract of WO 00/51568.
Derwent Abstract of FR 2781152.

* cited by examiner

*Primary Examiner*—S. Tran
(74) *Attorney, Agent, or Firm*—Young & Thompson

(57) ABSTRACT

The subject of the invention is an orodispersible solid pharmaceutical form characterized in that it comprises:
granules consisting of lactose and starch which have been codried;
at least one active substance.

Figure 1:
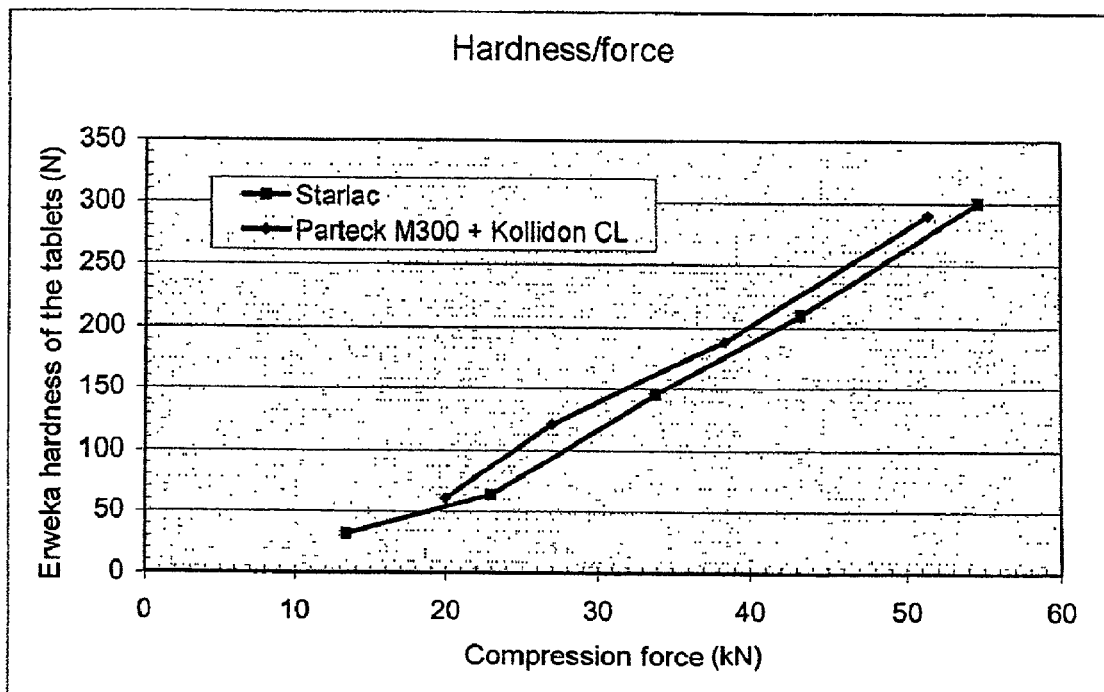
Figure 2:
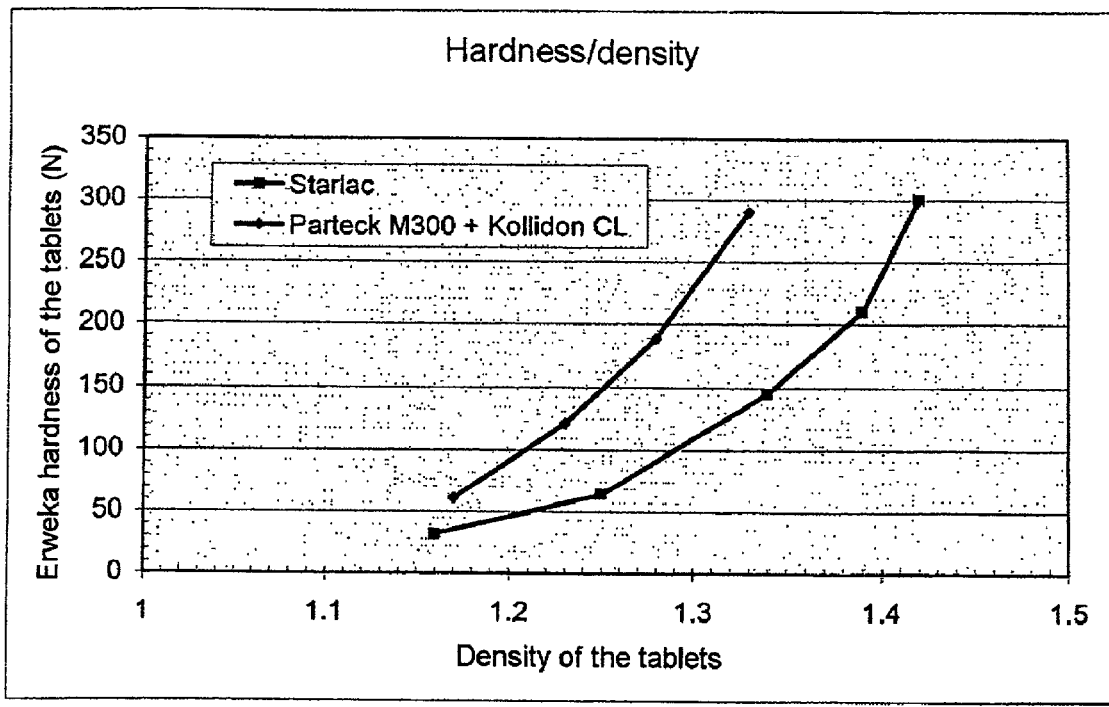
Figure 3:
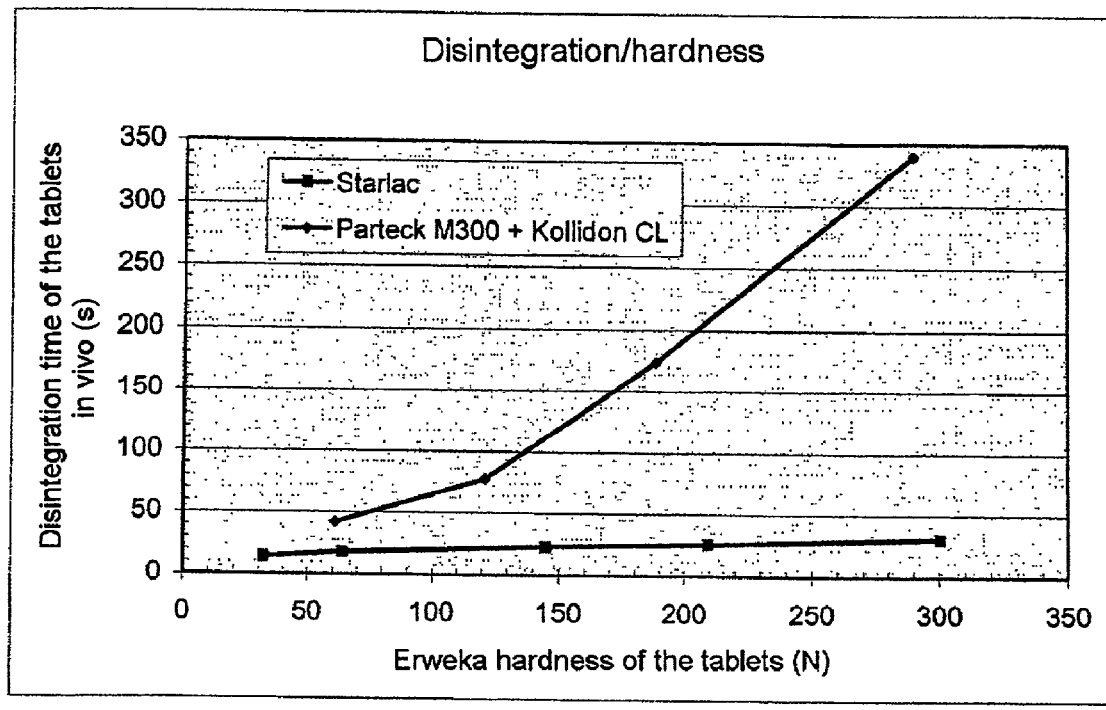
Figure 4:
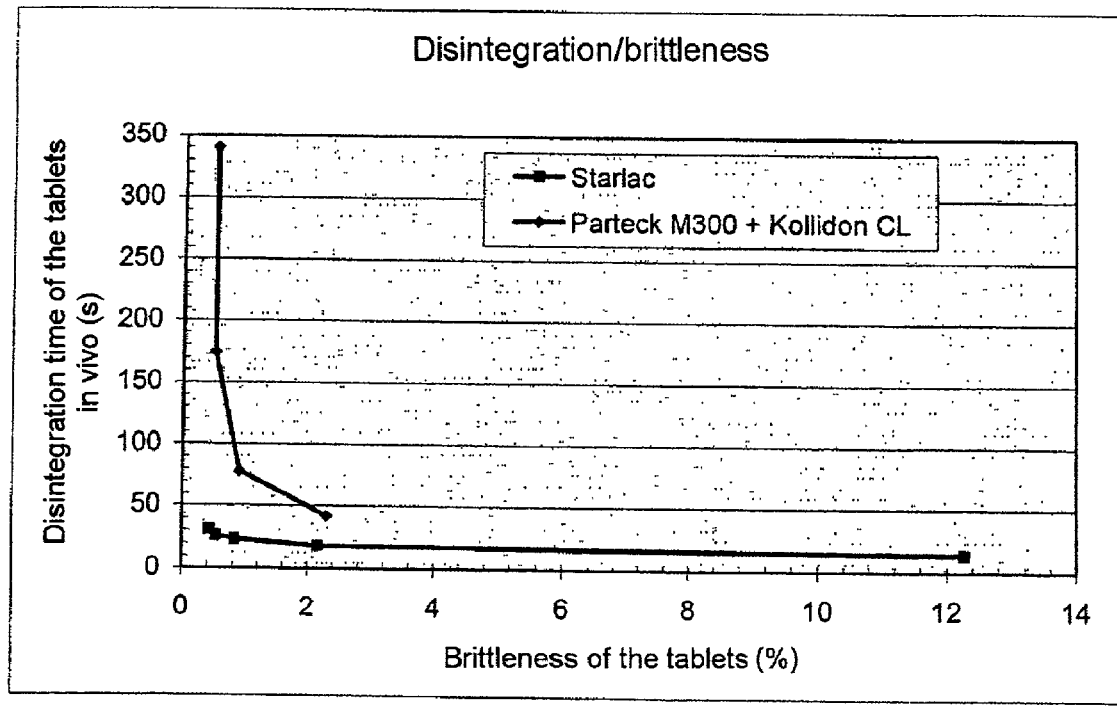
Figure 5:
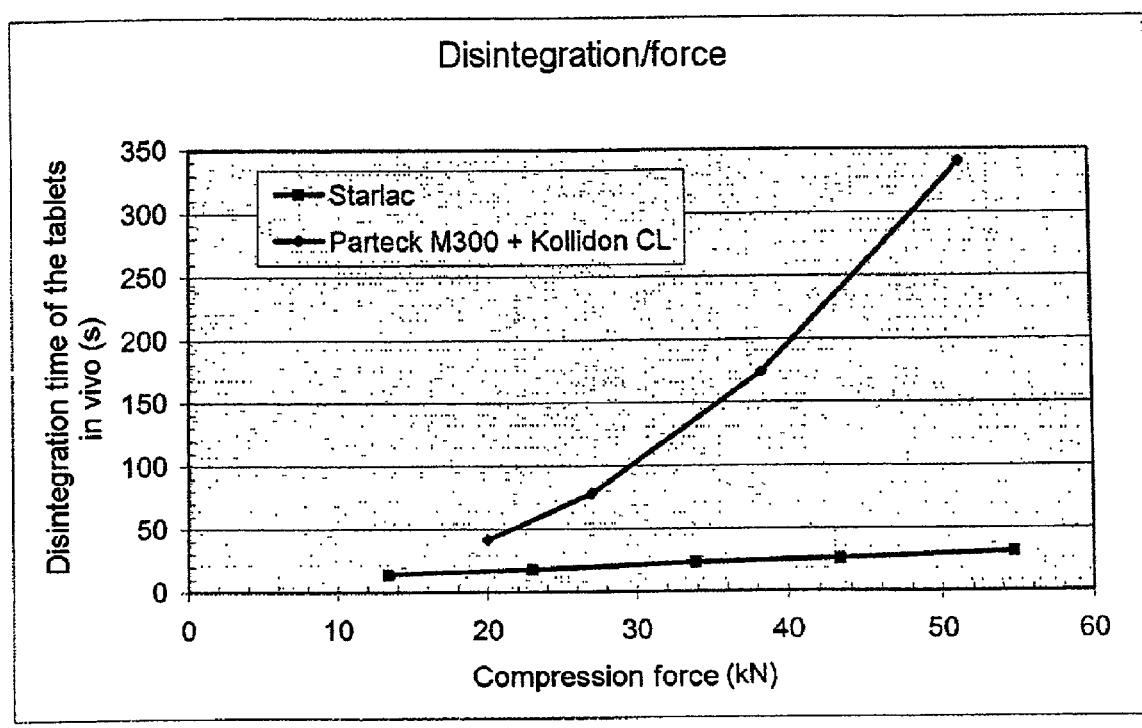

The subject of the invention is also the use of codried granules consisting of lactose and starch for the preparation of orodispersible solid pharmaceutical forms.

9 Claims, 3 Drawing Sheets

ORODISPERSIBLE SOLID PHARMACEUTICAL FORM

FIELD OF THE INVENTION

The subject of the invention is a solid pharmaceutical form which disintegrates rapidly in the mouth.

More precisely, the subject of the invention is an orodispersible pharmaceutical form comprising at least one active substance and a particular excipient.

Even though the European Pharmacopoeia 2001 does not yet list the orodispersible dosage form among the numerous existing galenic dosage forms, the term "orodispersible tablet" is now accepted. It corresponds to the following definition:

"Tablet which, when placed in the mouth, disperses rapidly therein before swallowing it" (Pharmeuropa, Vol. 10, No. 4, December 1998, p. 547, the content of which is herein incorporated by reference).

The orodispersible dosage form has the characteristic feature of requiring neither water nor chewing during its administration. It disintegrates in the presence of saliva, generally in less than a minute.

In the design of orodispersible dosage forms, two dosage forms can be produced:
  the dosage forms which break down: obtained most often by freeze-drying, these very porous dosage forms contain soluble excipients whose dissolution causes the breakdown of the structure.
  the dosage forms which explode: obtained by compression, the mechanism involved in the disintegration of these dosage forms in the mouth is ascribed to the disintegrating agents which they contain.

In the present invention, there is interest only in the dosage forms obtained by compression, and more particularly in the dosage forms obtained by direct compression.

BACKGROUND OF THE INVENTION

Numerous oral dosage forms are currently commercially available but they do not always meet the convenience of users: tablets for swallowing require the taking of water, gums and tablets for chewing involve use of the teeth.

Many people have difficulties swallowing conventional tablets which are often of non negligible size. The problems linked to the taking of medicaments (breathlessness, suffocation by obstruction of the throat) are often responsible for poor compliance with the dosages, or even a stopping of the treatment. These problems relate in particular to children, elderly persons, patients suffering from deglutition disorders or pathologies affecting saliva secretion.

The orodispersible dosage forms attempt to overcome these disadvantages by their simple mode of administration. By virtue of a rapid disintegration, which is possible in the presence of saliva, the orodispersible tablet is reduced, within a few tens of seconds after its administration, to small size aggregates which are easy to swallow. In the case of the formulation of a dosage form with immediate release of active agent, oral dispersion allows a more rapid availability in the body compared with the dosage forms to be swallowed by increasing the surface area for exchange with physiological fluids. An increased bioavailability of the active agent results therefrom.

Oral dispersibility does not correspond to a single phenomenon. The mechanism of disintegration is thought to have several origins, which are the swelling of a disintegrating agent in the presence of saliva, the development of a capillary network promoted by the presence of pores in the tablet, the tendency for the particles to return to their initial form, the heat released by the wetting of the constituents which increases the air pressure, and the repulsive force between the particles in contact with water. Regardless of the theory involved, the penetration of water is the first phase of the disintegration. The constituents of the orodispersible tablets should therefore promote it or at least not hinder it. In terms of formulation and manufacture, this therefore involves finding a compromise between the physical characteristics of the tablet and the chemical properties of the excipients.

Numerous rapidly dissolving dosage forms are described in the prior art. U.S. Pat. No. 5,464,632 describes a technology based on the film-coating of the active ingredient, which is intended not only to mask the taste of the active molecules but also to create an insoluble coating enhancing the rate of disintegration of the tablet. Indeed, the solubilization of the excipients at the surface constitutes a brake on the penetration of water into the tablets by increasing the viscosity of the incoming liquid. The formula uses a diluent (polyols), a disintegrating agent (crosslinked polyvinylpyrrolidone) and lubricants and customary adjuvants.

The document PCT/FR00/00495 (WO 00/51568) describes the use of hydrophobic lubricants whose negative action on the penetration of water is compensated by the use of a permeabilizing agent such as silica, in order to increase the affinity of the tablets for water. The formula also comprises a diluent and a disintegrating agent.

Document WO 00/57857 describes, for its part, the use of an effervescent agent coupled with a disintegrating agent so as to enhance the disintegration in the mouth. The formula comprises, in addition, a diluent which is not directly compressible.

Finally, the document FR 98/09221 (FR 2,781,152) describes a technology based on the synergy between a disintegrating agent and a type C acrylic polymer which leads to a considerably enhanced rate of disintegration.

All these technologies have in common the use of at least one disintegrating agent also called "superdisintegrant". This term groups together compounds whose disintegrating power is high. Among the most efficient, there are in particular KOLLIDON® CL (crosslinked polyvinylpyrrolidone marketed by BASF), EXPLOTAB® (carboxymethylated starch marketed by PENWEST), and AC DI SOL® (crosslinked carboxymethylcellulose sodium marketed by FMC). This superdisintegrant agent is essential in the formulation of orodispersible tablets, and should be used together with a direct compression excipient.

The formulator is then forced to prepare physical mixtures of different excipients necessary for the formulation of orodispersible tablets. However, the physical mixtures impose strict constraints on their production and their handling to ensure homogeneity of the mixture and the absence of demixing, properties which are essential in practice for obtaining tablets of constant quality, and these mixtures do not make it possible to prepare tablets of variable hardness as a function of the intended application. Indeed, the results obtained with such mixtures give rise to tablets of very high hardness, completely unsuitable for a rapid disintegration in the buccal cavity.

SUMMARY OF THE INVENTION

The aim of the invention is therefore to remedy this disadvantage and to provide an orodispersible solid pharmaceutical dosage form, having a pleasant texture, while using a simple excipient, of natural origin, which disintegrates rapidly in the mouth, and having an advantageous taste neutrality.

The Applicant has had the merit of finding that this aim could be achieved if a particular excipient capable of serving simultaneously as binder, disintegrant and diluent is used to prepare the said solid dosage form, while allowing the preparation of solid dosage forms over a wide range of hardness.

DETAILED DESCRIPTION OF THE INVENTION

The subject of the invention is therefore an orodispersible solid pharmaceutical form characterized in that it comprises:
- granules consisting of lactose and starch which have been codried;
- at least one active substance.

The subject of the invention is also the use of granules consisting of lactose and starch which have been codried for the preparation of orodispersible solid pharmaceutical dosage forms.

The expression solid pharmaceutical dosage form is understood to mean for the purposes of the invention any preparation in the form of tablets, which are obtained by densification of a powder. These solid dosage forms essentially consist of inert materials grouped under the term of excipients, and comprise one or more pharmaceutical active substances.

The term "orodispersible" is understood to mean solid dosage forms which disintegrate in the buccal cavity in less than 3 minutes, and preferably in less than one minute.

The said granules contained in the solid dosage forms in accordance with the invention correspond to the compositions described in Patent Application EP 00/402159.8 of which the Assignee is proprietor, and in its US counterpart, U.S. Ser. No. 09/905,596, now U.S. Pat. No. 6,770,368, the contents of which are herein incorporated by reference. These granules are characterized by a spherical structure and an advantageous compressiblity and are marketed under the name STARLAC® by the Assignee and by the company MEGGLE GmbH.

The disintegrating properties of the said granules are known for tablets placed in large volumes of liquid, with stirring. It is particularly surprising that such granules used for the manufacture of orodispersible dosage forms can give particularly satisfactory results in terms of disintegration in the mouth, this being for two reasons.

The first is based on the observation that the excipients least soluble in water are the most appropriate for the formulation of orodispersible tablets (solubilization, causing an increase in the viscosity of the water, is a brake on its penetration into the tablets). However, the said granules comprise a large fraction of lactose which is very soluble in water. Furthermore, the starch included in the said granules is not a "superdisintegrant" agent as used and described in the orodispersible dosage forms of the prior art.

The second is based on the observation that the disintegration properties of an excipient (used in a tablet), evaluated in water by conventional methods, cannot be extrapolated to the behavior of the same tablet in vivo, in saliva. Indeed, the rates of disintegration in water are measured (according to the European Pharmacopoeia) in a quantity of water which is sufficiently large not to reach saturation in terms of solubilization, whereas "in vivo", by virtue of the small volume of saliva, the excipients are at saturation. Furthermore, the stirring to which the tablets are subjected during the customary test does not reflect the disintegration in the mouth. The Applicant has thus observed during comparative trials that some excipients known as good disintegrants were not suitable for the preparation of orodispersible dosage forms. Conversely, some excipients which disintegrate moderately in water can have advantageous properties in vivo.

The Applicant then found that the said granules surprisingly conferred on the tablets very good capacities to disintegrate in the mouth, this being for a wide range of tablet hardness, while preserving low brittleness which is particularly remarkable. Indeed, most of the orodispersible dosage forms of the prior art which disintegrate rapidly in the mouth are very brittle, which results in disintegration of the tablet as soon as it is handled and removed from its packaging.

The orodispersible pharmaceutical dosage form according to the invention, that is to say which disintegrate in the mouth in less than one minute, advantageously has a brittleness of less than 2%, and preferably less than or equal to 1%. This brittleness is measured according to the pharmaceutical technical method 2.9.7 of the European Pharmacopoeia, $3^{rd}$ edition (available from European Directorate for the Quality of Medecines EDQM, European Pharmacopoeia, 226 avenue de Colmar BP 907, F-67029 Strasbourg Cedex 1, FRANCE; www.pheur.org), the content of which is herein incorporated by reference.

It is particularly remarkable that the above-mentioned criteria of orodispersibility and brittleness are observed for a wide range of tablet hardness, that is to say for tablets having a hardness, measured with an ERWEKA TBH 30 GMD type durometer, of between 30 and 300 newtons.

The orodispersible pharmaceutical dosage forms according to the invention therefore constitute, for the reasons which have just been disclosed, a novel industrial product.

To prepare these pharmaceutical dosage forms according to the invention, the procedure is carried out as follows or in an equivalent manner.

The desired active substance(s) is (are) first of all selected. These active substances may be chosen from a large number of pharmaceutical active agents intended for oral administration, and in particular from the group consisting of analgesics, antipyretics, antidiarrhoeals, antispasmodics, antiinfectious agents, antibiotics, antivirals, antiparasitics, digestive motility regulators, blood pressure regulators, cardiac and coronary insufficiency regulators, cardiac rhythm regulators, central nervous system regulators, lipid, carbohydrate and protein metabolism regulators, bone metabolism regulators, vasculoprotective and venotonic agents, hormone and immune system regulators, steroidal and nonsteroidal anti-inflammatory agents, antihistamines and anti-allergics, antiasthmatics, antitusives, expectorants, mucoregulators, antiemetics, diuretics, laxatives, cytotoxics and cytostatics, vitamin and mineral elements, plant extracts.

In some cases, it is possible to advantageously mask the bitterness or the unpleasant taste of the active substance, or alternatively to modify its adsorption by film-coating or hard-coating the said active substance. Film-coating may be carried out with various taste-masking agents known to a person skilled in the art, such as, in particular, cellulosic polymers (ethyl cellulose, hydroxyethyl cellulose, hydroxypropyl methyl cellulose, hydroxypropyl cellulose, cellulose acetate, cellulose acetophthalate), polymethacrylates marketed under the name EUDRAGIT®, mixtures of cellulosic polymers and other polymers such as, for example, polyvinylpyrrolidone marketed under the name KOLLIDON®, all these polymers or mixtures thereof being optionally combined with plasticizers such as in particular polyethylene glycol.

The film-coating of the active substance is carried out according to a known process such as, for example, the fluidized bed process, in a turbine mixer, coacervation, microencapsulation, extrusion-spheronization.

Although less common, it is also possible to use hard-coating as a technique for coating the active substance. It is carried out according to processes known to a person skilled in the art, using various sugars or polyols optionally mixed with film-forming polymers.

The quantity of active substance present in the solid dosage form according to the invention depends on the active agent chosen. Generally, it represents 0.2 to 95%, and preferably 1 to 50% by weight of the solid dosage form.

This active substance is mixed with the excipient consisting of starch and lactose granules.

Preferably, these granules have a lactose/starch ratio of between 90/10 and 25/75 and still more preferably between 85/15 and 50/50.

These granules may be obtained according to several variants, and in particular by codrying. Preferably, the said granules are obtained by co-spray-drying lactose and starch, according to a process described in the abovementioned patent applications.

The proportions of the said granules in the solid dosage form according to the invention vary according to the type of medicament which it is desired to prepare. In general, these granules represent from 20 to 99%, preferably 40 to 98% by weight of the said solid dosage form.

It is also possible to cause the mixture thus prepared to contain one or more compounds consisting of flavourings, lubricants, colourings and sweeteners.

The said mixture is then formed by densification of the powder. In particular, this operation may be carried by direct compression.

The solid dosage forms thus obtained have an orodispersibility which is quite remarkable, regardless of their hardness and density. Indeed, the use of lactose and starch granules in accordance with the invention allows the formulator to choose from a very broad panel of parameters for manufacturing solid dosage forms while being assured to finally obtain a dosage form which is not very brittle, which disintegrates very rapidly in the mouth, which was not allowed by the prior art excipients intended for fast release dosage forms. Furthermore, the properties of the said granules allow the formulator to dispense with the addition of a superdisintegrant to the tablet formula, which is very advantageous from the technical and economic point of view. The use according to the invention of codried granules consisting of lactose and starch in the manufacture of orodispersible dosage forms which disintegrate in the mouth in less than one minute is therefore particularly innovative.

The invention will be understood more clearly on reading the examples which follow and the figure relating thereto, intended to illustrate, without limitation, advantageous embodiments and to demonstrate the superiority, relative to the prior art, of the solid dosage forms in accordance with the invention.

EXAMPLE 1

Preparation of Solid Dosage Forms According to the Invention

Tablets according to the invention, of variable hardness and weight, are prepared whose disintegration time in the mouth is measured. This disintegration time corresponds to the time necessary for the entire suspension derived from the disintegration of the tablet placed in the mouth to be swallowed (the deglutition time is an integral part of the disintegration time in order to take into account possible cases where an excessively high hygroscopicity could hinder the deglutition through lack of saliva).

The disintegration time is measured by exact timing: the timer is started as soon as the tablet is placed in the mouth, it is stopped when the whole suspension has been swallowed.

The hardness of the various tablets obtained is measured using an ERWEKA TBH 30GMD type durometer.

Various active substances are used: paracetamol, ibuprofen, vitamin C.

To prepare the tablets, a FETTE EXACTA 21 type press equipped with flat dies is used.

a) Paracetamol Tablets.

TABLE 1

| Constituents | Percentage formula | Unit formula |
| --- | --- | --- |
| Coated paracetamol (RHODAPAP NCR) | 53.76% | 537.6 mg |
| STARLAC ® | 44.44% | 444.4 mg |
| Red fruit flavouring | 1.00% | 10.0 mg |
| Aspartame | 0.30% | 3.0 mg |
| Magnesium stearate | 0.5% | 5.0 mg |
| TOTAL | 100 | 1 000 mg |

Characteristics of the tablets:
diameter=16 mm
weight=1 g
Erweka hardness=45N
Disintegration time in the mouth <30 seconds b) Ibuprofen Tablets.

TABLE 2

| Constituents | Percentage formula | Unit formula |
| --- | --- | --- |
| Ibuprofen coated with fat (70% active substance final) | 23.82% | 142.9 mg |
| STARLAC ® | 73.18% | 439.1 mg |
| Red fruit flavouring | 2.00% | 12.0 mg |
| Aspartame | 0.5% | 3.0 mg |
| Magnesium stearate | 0.5% | 3.0 mg |
| TOTAL | 100% | 600.0 mg |

Characteristics of the tablets:
diameter=13 mm
weight=600 mg
Erweka hardness=40N
Disintegration time in the mouth <20 seconds

TABLE 3

| Constituents | Percentage formula | Unit formula |
|---|---|---|
| Ibuprofen coated with polysaccharide (90% active substance final) | 18.52% | 111.1 mg |
| STARLAC ® | 78.48% | 470.9 mg |
| Red fruit flavouring | 2.00% | 12.0 mg |
| Aspartame | 0.50% | 3.0 mg |
| Magnesium stearate | 0.5% | 3.0 mg |
| TOTAL | 100% | 600.0 mg |

Characteristics of the tablets:
diameter=13 mm
weight=600 mg
Erweka hardness=30N
Disintegration time in the mouth <20 seconds c) Vitamin C Tablets.

TABLE 4

| Constituents | Percentage formula | Unit formula |
|---|---|---|
| Vitamin C | 25% | 100 mg |
| STARLAC ® | 74.5% | 298 mg |
| Magnesium stearate | 0.5% | 2.0 mg |
| TOTAL | 100% | 400.0 mg |

Characteristics of the tablets:
diameter=10 mm
weight=400 mg
Erweka hardness=80N
Disintegration time in the mouth=30 seconds CONCLUSION: Regardless of the characteristics of the tablets in terms of hardness, weight, diameter, the disintegration time in the mouth is always low, less than 40 seconds, even for high hardness. This is particularly advantageous because high hardness of tablets allow their handling with no risk of impairment.

EXAMPLE 2

Preparation of Solid Dosage Forms According to the Invention and Comparison with a Composition of the Prior Art A formula according to the invention (STARLAC®+ lubricant) is compared with a formula according to the prior art (mannitol for direct compression+disintegrating agent+ lubricant) in order to prepare orodispersible dosage forms.

The compression is carried out on a FETTE EXACTA 21 press equipped with flat dies having a diameter of 16 mm with bevelled edges.

The various characteristics of the tablets obtained are measured:
average weight
average thickness
density
Erweka hardness
brittleness according to the European Pharmacopoeia ($3^{rd}$ edition, technical method 2.9.7.)
disintegration time in the mouth
compression force necessary to obtain the tablet Formula According to the Invention:
STARLAC®: 99.4%
Magnesium stearate: 0.6%
Mixing: 5 minutes in a TURBULA mixer Formula According to the Prior Art:
Mannitol PARTECK®M300 (MERCK): 95.0%
KOLLIDON®CL (BASF): 3.0%
Magnesium stearate: 2.0%
Mixing in a TURBULA for 5 minutes without lubricant, and then for 5 minutes with the lubricant.

The characteristics of the various tablets are given in the tables below:

TABLE 5

| Tablets according to the invention | Trial 1 | Trial 2 | Trial 3 | Trial 4 | Trial 5 |
|---|---|---|---|---|---|
| Average weight (mg) | 929 | 1 009 | 1 069 | 1 113 | 1 135 |
| Coefficient of variation (%) | 0.16 | 0.07 | 0.08 | 0.10 | 0.08 |
| Average thickness (mm) | 4.00 | 4.00 | 3.98 | 3.99 | 3.98 |
| Coefficient of variation (%) | 0.06 | 0.05 | 0.09 | 0.05 | 0.05 |
| Density | 1.160 | 1.250 | 1.340 | 1.390 | 1.420 |
| Erweka hardness | 32.1 | 64.1 | 145.2 | 209.7 | 300.5 |
| Coefficient of variation (%) | 17.83 | 5.65 | 6.13 | 4.52 | 2.20 |
| Brittleness (%) | 12.28 | 2.17 | 0.84 | 0.54 | 0.44 |
| Disintegration time in the mouth (s) | 14 | 18 | 23 | 26 | 31 |
| Compression force (kN) | 13.4 | 23 | 33.9 | 43.3 | 54.7 |

TABLE 6

| Tablets according to the prior art | Trial 6 | Trial 7 | Trial 8 | Trial 9 |
|---|---|---|---|---|
| Average weight (mg) | 946 | 991 | 1 036 | 1 074 |
| Coefficient of variation (%) | 0.21 | 0.39 | 0.20 | 0.23 |
| Average thickness (mm) | 4.01 | 4.00 | 4.01 | 4.01 |
| Coefficient of variation (%) | 0.11 | 0.04 | 0.09 | 0.10 |
| Density | 1.170 | 1.230 | 1.280 | 1.330 |
| Erweka hardness | 61.1 | 121.1 | 188.6 | 289.9 |
| Coefficient of variation (%) | 6.67 | 18.88 | 13.29 | 5.33 |
| Brittleness (%) | 2.3 | 0.90 | 0.50 | 0.50 |
| Disintegration time in the mouth (s) | 42 | 78 | 174 | 340 |
| Compression force (kN) | 20.0 | 27.0 | 38.4 | 51.4 |

It is evident from the comparison of the two formulations that:
the compressibility of the two formulas is equivalent (this is illustrated by FIG. 1)
regardless of the characteristics of the tablet manufactured with the composition according to the invention (applied compression force, hardness, density, brittleness), the disintegration time in the mouth is always low (less than 40 seconds) and practically constant, which is quite remarkable. This is illustrated by FIGS. 2, 3, 4 and 5.
That the composition according to the invention allows the production of a tablet with very fast disintegration, having high hardness and low brittleness (<1%). These characteristics allow the handling of the tablet under standard conditions, with no risk of crumbling, which is not the case for tablets of the prior art which have low hardness and high brittleness so as to preserve fast disintegration in the mouth.

Experimental Procedure to Measure Brittleness (method 2.9.7. of the European Pharmacopoeia)

Apparatus

Use a rotary drum with an inside diameter of 283 mm to 291 mm and a height of 36 mm to 40 mm, consisting of a transparent synthetic polymer with polished internal surfaces which do not generate any static electricity. One of the drum faces is removable. Upon each rotation, the tablets are projected from the drum center towards the external wall, following a curved trajectory with an inside radius between 75.5 mm and 85.5 mm. The drum is mounted on the horizontal shaft of a driving device whose rotation speed is from 25±1 RPM. Consequently, upon each rotation, the tablets will roll or slide and fall onto the wall or one upon the other.

Method of Operation

In the case of tablets having a unit mass lower than or equal to 0.65 g, pick up a sample of 20 tablets; in the case of tablets having a larger unit mass, pick up 10 tablets. Place the tablets on a Nr 1000 sieve and remove the free dust particles by means of compressed air or a soft brush. Accurately weigh the tablets and place them into the drum. Perform 100 rotations, then take the tablets out of the drum. Remove the free dust particles as stated above. If there are no cracked, fissured or broken tablets, weigh with an accuracy of one milligram.

As a general rule, the test is carried out only once. However, should the results prove questionable or if the mass loss is higher than one percent, repeat the test twice and calculate the average of 3 tests.

The invention claimed is:

1. A compressed orodispersible solid pharmaceutical composition in a solid dosage form having a ERWEKA hardness of between 30 and 300 newtons, comprising:
    spherical granules consisting essentially of co-spray-dried lactose and granular starch, wherein the lactose/starch ratio is between 90/10 and 25/75, said granules having a friability of less than or equal to 80%, according to a test A;
    at least one pharmaceutically active substance, and
    wherein said composition disintegrates in the mouth in less than one minute and has a brittleness of less than 2%, and
    wherein the said granules represent 20 to 99% by weight of said solid dosage form.

2. The solid form of claim 1, wherein the said granules represent 40 to 98% by weight of the said solid dosage form.

3. The solid form of claim 1, wherein the said granules have a lactose/starch ratio of 85/15 to 50/50.

4. The solid form of claim 1, wherein said pharmaceutically active substance is selected from the group consisting of analgesics, antipyretics, antidiarrhoeals, antispasmodics, antiinfectious agents, antibiotics, antivirals, antiparasitics, digestive motility regulators, blood pressure regulators, cardiac and coronary insufficiency regulators, cardiac rhythm regulators, central nervous system regulators, lipid, carbohydrate and protein metabolism regulators, bone metabolism regulators, vasculoprotective and venotonic agents, hormone and immune system regulators, steroidal and nonsteroidal anti-inflammatory agents, antihistamines and antiallergics, antiasthmatics, antitusives, expectorants, mucoregulators, antiemetics, diuretics, laxatives, cytotoxics and cytostatics, vitamin and mineral elements, plant extracts.

5. The solid form of claim 1, wherein said pharmaceutically active substance represents 0.2 to 95 by weight of the solid dosage form.

6. The solid form of claim 5, wherein said pharmaceutically active substance represents 1 to 50% by weight of the solid dosage form.

7. The solid form of claim 1, wherein said pharmaceutically active substance is coated by film-coating or hard-coating.

8. The solid form of claim 1, which has a brittleness of less than or equal to 1%.

9. A process for the manufacture of orodispersible pharmaceutical solid forms which contain a pharmaceutically active substance, and which disintegrate in the mouth in less than one minute, wherein the active substance is mixed with the spherical granules of lactose and starch according to claim 1, and wherein said mixture is formed into a solid form, having a ERWEKA hardness of between 30 and 300 newtons, and wherein said form has a brittleness of less than 2%.

* * * * *